US011589897B2

(12) United States Patent
Cornelius et al.

(10) Patent No.: US 11,589,897 B2
(45) Date of Patent: Feb. 28, 2023

(54) IMPLANTABLE MONITOR INTRODUCER DESIGN FEATURES

(71) Applicant: Cardiac Pacemakers, Inc., St. Paul, MN (US)

(72) Inventors: Kathryn Cornelius, Hudson, WI (US); David P. Stieper, North Branch, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 617 days.

(21) Appl. No.: 16/665,963

(22) Filed: Oct. 28, 2019

(65) Prior Publication Data

US 2020/0129206 A1 Apr. 30, 2020

Related U.S. Application Data

(60) Provisional application No. 62/751,681, filed on Oct. 28, 2018.

(51) Int. Cl.
*A61B 17/34* (2006.01)
*A61B 17/00* (2006.01)

(52) U.S. Cl.
CPC .... *A61B 17/3468* (2013.01); *A61B 17/00234* (2013.01); *A61B 2560/04* (2013.01)

(58) Field of Classification Search
CPC .............. A61B 17/34; A61B 17/34209; A61B 17/00234; A61B 17/3468; A61B 2560/04

USPC ............................. 606/99–100, 167; 604/36
See application file for complete search history.

(56) References Cited

U.S. PATENT DOCUMENTS

| 8,435,305 | B2 * | 5/2013 | Lozier | A61F 2/28 |
| | | | | 606/86 R |
| 10,786,279 | B2 * | 9/2020 | Vanderpool | A61B 17/3468 |
| 2007/0249992 | A1 * | 10/2007 | Bardy | A61M 37/0069 |
| | | | | 604/60 |
| 2010/0094252 | A1 * | 4/2010 | Wengreen | A61B 17/3468 |
| | | | | 604/218 |
| 2010/0324578 | A1 * | 12/2010 | Bardy | A61M 37/0069 |
| | | | | 606/167 |
| 2010/0331868 | A1 * | 12/2010 | Bardy | A61M 37/0069 |
| | | | | 606/167 |
| 2014/0276928 | A1 * | 9/2014 | Vanderpool | A61B 17/3468 |
| | | | | 606/129 |
| 2017/0049467 | A1 * | 2/2017 | Foster | A61B 17/3468 |
| 2017/0296229 | A1 * | 10/2017 | Sick | A61B 17/32093 |
| 2017/0296230 | A1 * | 10/2017 | Dubeau | A61B 17/3468 |

* cited by examiner

*Primary Examiner* — Jessica Weiss
(74) *Attorney, Agent, or Firm* — Faegre Drinker Biddle & Reath LLP

(57) ABSTRACT

Various aspects of the present disclosure are directed toward introducer apparatuses, systems, and methods for positioning an implantable medical device within a patient. The introducer may include a housing having a proximal opening and a distal opening and configured to position the implantable medical device adjacent the distal opening prior to ejection and an ejection rod configured to pass through the proximal opening and eject the implantable medical device from the housing through the distal opening of the housing.

17 Claims, 6 Drawing Sheets

IMPLANTABLE MONITOR INTRODUCER DESIGN FEATURES

CROSS-REFERENCE TO RELATED APPLICATION

This application claims priority to Provisional Application No. 62/751,681, filed Oct. 28, 2018, which is herein incorporated by reference in its entirety.

TECHNICAL FIELD

The present disclosure relates to medical devices and methods for creating a pocket in a patient for an implantable medical device. More specifically, the disclosure relates to devices and methods for facilitating implantation of the implantable medical device under the patient's skin in a minimally-invasive and efficient manner.

BACKGROUND

Medical devices may be implanted subcutaneously under a patient's skin with minimal intervention and without the deeply positioning the device in the patient's body. Positioning of the medical device may be difficult due to high insertion forces necessary to manipulate the medical device and form a pocket for the device under the patient's skin. Improperly positioning functional aspects of the device may result in poor performance.

SUMMARY

In Example 1, an introducer apparatus for positioning an implantable medical device within a patient includes a housing having a proximal opening and a distal opening and configured to position the implantable medical device adjacent the distal opening prior to ejection; and an ejection rod configured to pass through the proximal opening and eject the implantable medical device from the housing through the distal opening of the housing.

In Example 2, further to the apparatus of Example 1, the housing is configured to maintain the implantable medical device adjacent the distal opening and release the implantable medical device in response to a force applied by the ejection rod.

In Example 3, further to the apparatus of any one of Examples 1-3, the housing includes a stop, comprising one or more raised surfaces, configured to position the implantable medical device adjacent the distal opening prior to ejection.

In Example 4, further to the apparatus of Example 3, the housing includes a proximal portion including the proximal opening and a distal portion including the distal opening, the proximal portion and the distal portion separating an intermediate portion sized to contain the implantable medical device, and the intermediate portion includes a first surface and a second surface, and one of the first surface and the second surface includes the stop.

In Example 5, further to the apparatus of any one of Examples 3-4, the stop includes two curved surfaces.

In Example 6, further to the apparatus of any one of Examples 3-5, the apparatus also includes an inserter arranged at and extending from a distal portion of the housing and the stop is configured to hold the implantable medical device adjacent the inserter and release the medical device in response to a force applied by the ejection rod.

In Example 7, further to the apparatus of Example 4, the stop is configured to maintain positioning of the ejection rod within the housing prior to loading of the implantable medical device.

In Example 8, further to the apparatus of Example 7, the stop is configured to maintain a distal portion of the ejection rod adjacent the distal opening prior to withdrawn of the ejection rod toward the proximal opening for loading of the implantable medical device.

In Example 9, further to the apparatus of Example 8, the stop includes two raised surfaces and the two raised surfaces are configured to maintain a distal portion of the ejection rod between the raised surfaces prior to withdrawn of the ejection rod toward the proximal opening for loading of the implantable medical device.

In Example 10, further to the apparatus of any one of Examples 3-9, the stop includes two curved surfaces and one of the curved surfaces has a greater height than the other of the curved surfaces.

In Example 11, further to the apparatus of any one of Examples 6-10, the stop is configured to bias the implantable medical device toward the inserter in response to the force applied by the ejection rod to release the implantable medical device through the distal opening of the housing.

In Example 12, further to the apparatus of Example 11, the stop is arranged along one of the first surface and the second surface and the inserter is arranged along another of the one of the first surface and the second surface.

In Example 13, further to the apparatus of any one of Examples 1-12, the ejection rod includes two laterally opposing surfaces tapering inwardly toward a longitudinally axis of the ejection rod.

In Example 14, further to the apparatus of Example 13, a bottom surface of the ejection rod is tapered inwardly reducing a diameter of the ejection rod.

In Example 15, further to the apparatus of any one of Examples claims 1-14, the housing includes a clip configured to release the implantable medical device within the housing in the pathway of the ejection rod. 16.

In Example 16, an introducer apparatus for positioning an implantable medical device within a patient, includes a housing having a proximal opening and a distal opening and an intermediate portion sized to contain the implantable medical device, the intermediate portion including a stop configured to position the implantable medical device adjacent the distal opening prior to ejection; and an ejection rod configured to pass through the proximal opening and eject the implantable medical device from the housing through the distal opening of the housing.

In Example 17, further to the apparatus of Example 16, the stop includes one or more raised surfaces configured to position the implantable medical device adjacent the distal opening prior to ejection.

In Example 18, further to the apparatus of Example 17, the intermediate portion includes a first surface and a second surface, and one of the first surface and the second surface includes the stop.

In Example 19, further to the apparatus of Example 18, wherein the stop is configured to maintain positioning of the ejection rod within the housing prior to loading of the implantable medical device.

In Example 20, further to the apparatus of Example 19, the stop is configured to maintain a distal portion of the ejection rod adjacent the distal opening prior to withdrawn of the ejection rod toward the proximal opening for loading of the implantable medical device.

In Example 21, further to the apparatus of Example 20, the stop includes two raised portions and the two raised portions are configured to maintain a distal portion of the ejection rod between the raised portions prior to withdrawn of the ejection rod toward the proximal opening for loading of the implantable medical device.

In Example 22, further to the apparatus of Example 18, the stop includes two curved surfaces and one of the curved surfaces has a greater height than the other of the curved surfaces.

In Example 23, further to the apparatus of Example 16, the apparatus also includes an inserter arranged at and extending from a distal portion of the housing and the stop is configured to hold the implantable medical device adjacent the inserter and release the medical device in response to a force applied by the ejection rod.

In Example 24, further to the apparatus of Example 16, the stop is configured to bias the implantable medical device toward the inserter in response to the force applied by the ejection rod to release the implantable medical device through the distal opening of the housing.

In Example 25, further to the apparatus of Example 16, the stop is configured to maintain the implantable medical device adjacent the distal opening and release the implantable medical device in response to a force applied by the ejection rod.

In Example 26 an introducer apparatus for positioning an implantable medical device within a patient includes a housing having a proximal opening and a distal opening and an intermediate portion sized to contain the implantable medical device, the intermediate portion including a stop configured to position the implantable medical device adjacent the distal opening prior to ejection; and an ejection rod including two laterally opposing surfaces tapering inwardly toward a longitudinally axis of the ejection rod and configured to pass through the proximal opening and eject the implantable medical device from the housing through the distal opening of the housing.

In Example 27, further to the apparatus of Example 26, a bottom surface of the ejection rod is tapered inwardly reducing a diameter of the ejection rod.

In Example 28, further to the apparatus of Example 27, the intermediate portion includes a first surface and a second surface, and the second surface includes the stop and the bottom surface of the ejection rod is adjacent the second surface of the intermediate portion of the housing.

In Example 29, further to the apparatus of Example 28, the apparatus also includes an inserter arranged at and extending from a distal portion of the housing and the stop is configured to hold the implantable medical device adjacent the inserter and release the medical device in response to a force applied by the ejection rod.

In Example 30, further to the apparatus of Example 29, the inserter is arranged along the first surface and the stop is configured to bias the implantable medical device toward the inserter in response to the force applied by the ejection rod to release the implantable medical device through the distal opening of the housing.

In Example 31, further to the apparatus of Example 30, a top surface of the ejection rod is substantially planar.

In Example 32, further to the apparatus of Example 26, the housing includes a clip configured to release the implantable medical device within the housing in the pathway of the ejection rod.

In Example 33, further to the apparatus of Example 26, the stop includes one or more raised surfaces configured to position the implantable medical device adjacent the distal opening prior to ejection.

In Example 34, a method includes arranging an implantable medical device within an introducer, the introducer include an ejection rod and a housing having a proximal opening and a distal opening and a stop; arranging the implantable medical device to contact the stop and adjacent to the distal opening; and passing the implantable medical device over the stop and from the housing through the distal opening of the housing.

In Example 35, the method of Example 34, the method also includes withdrawing the ejection rod distally from the stop prior to arranging the implantable medical device within the introducer.

While multiple embodiments are disclosed, still other embodiments of the present disclosure will become apparent to those skilled in the art from the following detailed description, which shows and describes illustrative embodiments of the subject matter disclosed herein. Accordingly, the drawings and detailed description are to be regarded as illustrative in nature and not restrictive.

Figure 1:
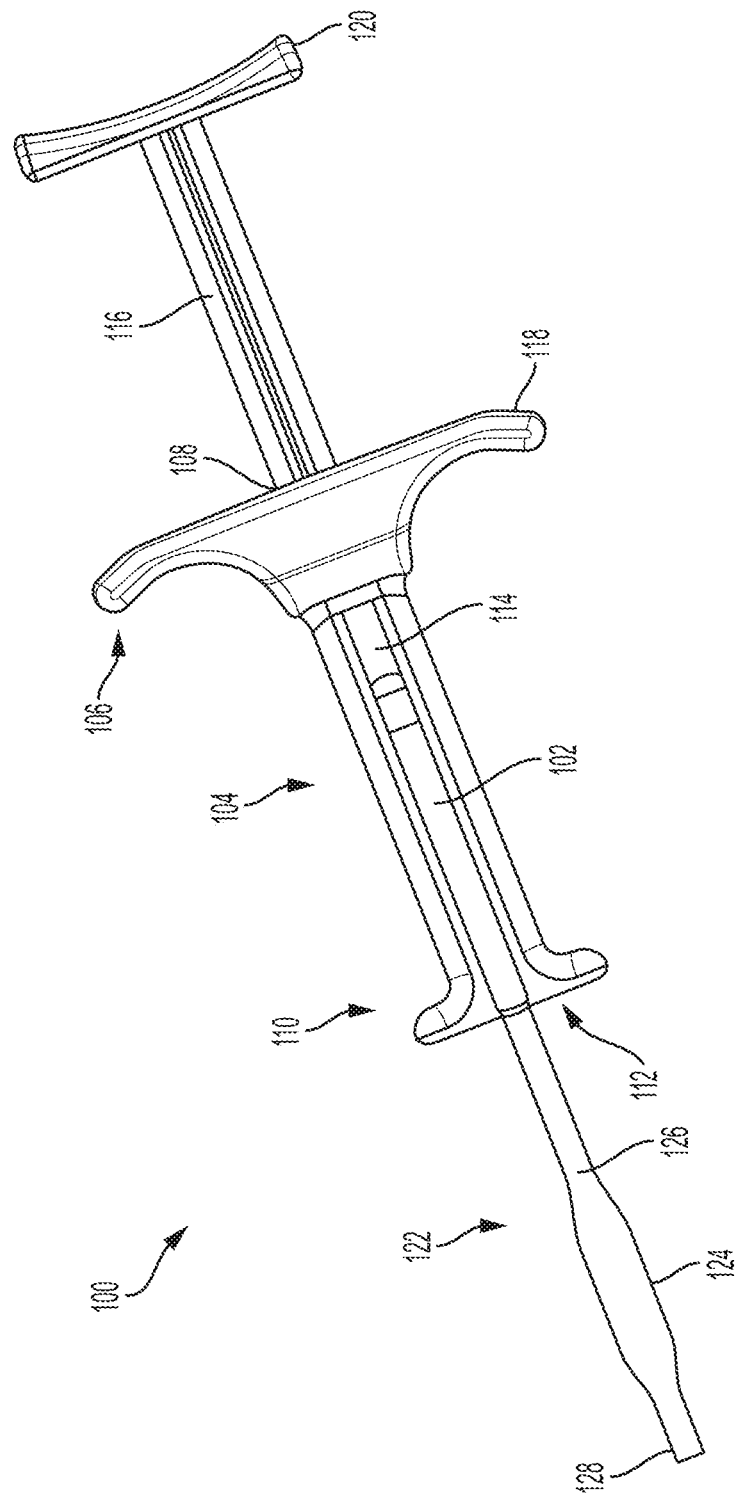
FIG. 1 shows an illustration of an exemplary introducer apparatus and an implantable medical device.

While the subject matter disclosed herein is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the subject matter disclosed herein as defined by the appended claims.

As used herein in association with values (e.g., terms of magnitude, measurement, and/or other degrees of qualitative and/or quantitative observations that are used herein with respect to characteristics (e.g., dimensions, measurements, attributes, components, etc.) and/or ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a value, configuration, orientation, and/or other characteristic that is equal to (or the same as) the stated value, configuration, orientation, and/or other characteristic or equal to (or the same as) a value, configuration, orientation, and/or other characteristic that is reasonably close to the stated value, configuration, orientation, and/or other characteristic, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

DETAILED DESCRIPTION

FIG. 1 shows an illustration of an exemplary introducer apparatus 100 and an implantable medical device 101. The introducer apparatus 100 includes a housing 104 having a proximal portion 106 including a proximal opening 108, and distal portion 110 including a distal opening 112. An intermediate portion 114 separates the proximal portion 106 and the distal portion 110. The intermediate portion 114 is sized and configured to contain the implantable medical device 102.

The introducer apparatus 100 is also provided with an ejection rod 116 that is configured to pass through the proximal opening 108, and configured to eject the implantable medical device 102 from the housing 104. The ejection rod 116 and housing 104 may function similar to a plunger, such that the implantable medical device 102 is ejected from the housing 104 in response to a user applying force to the ejection rod 116 in a direction that is longitudinally along the body of the ejection rod 116 or approximately parallel with the length of the housing 104. In certain instances, one or both of the housing 104 and/or the ejection rod 116 may include handles 118, 120. The handles 118, 120 allow for addition grip for a user in manipulating the housing 104 and/or the ejection rod 116.

The introducer apparatus 100 also may include an inserter 122 arranged at and extending from the distal portion 110 of the housing 104. The inserter 122 includes a distal tip 128 and an intermediate portion 124 having a greater width than the distal tip 128 of the inserter 122. As shown in FIG. 1, a portion 126 of the inserter 122 extending from the distal portion 110 of the housing 104 includes a width that is less than the width of the intermediate portion 124 of the inserter 122. In addition, the portion 126 of the inserter 122 extending from the distal portion 110 of the housing 104 may include a width that is approximately similar to or equal to the width of the distal tip 128 of the inserter 122. In certain instances, the distal tip 128 may taper distally inwardly from an upper surface, lower surface, side surface or any combination thereof. The intermediate portion 124 of the inserter 122 having a greater width may have a width that is 1%, 5%, 10%, 15%, 20%, 25%, 30%, 35%, 40%, 45%, or 50% greater (or any percentage in between) than the width of the other portions 126, 128 of the inserter 122. In addition, the intermediate portion 124 of the inserter 122 may have a width that is approximately similar to or approximately equal to the width of the implantable medical device 102.

The inserter 122 may be configured to create a pocket sized to surround the implantable medical device 102 within the patient. The implantable medical device 102 may be guided into the pocket in response to the ejection rod 116 ejecting the implantable medical device from the housing 104 through the distal opening 112. In creating a pocket in a patient, an incision may be made in a patient's skin. The incision may be made by a separate device, or may be made by the inserter 122. After the incision is made, the inserter 122 may be manipulated within the patient through the incision, and the pocket for the implantable medical device 102 is then formed. The pocket for the implantable medical device 102 may be formed as having asymmetric dimensions due to the intermediate portion 124 of the inserter 122 having a greater width than the other portions of the inserter 122.

Figure 2:
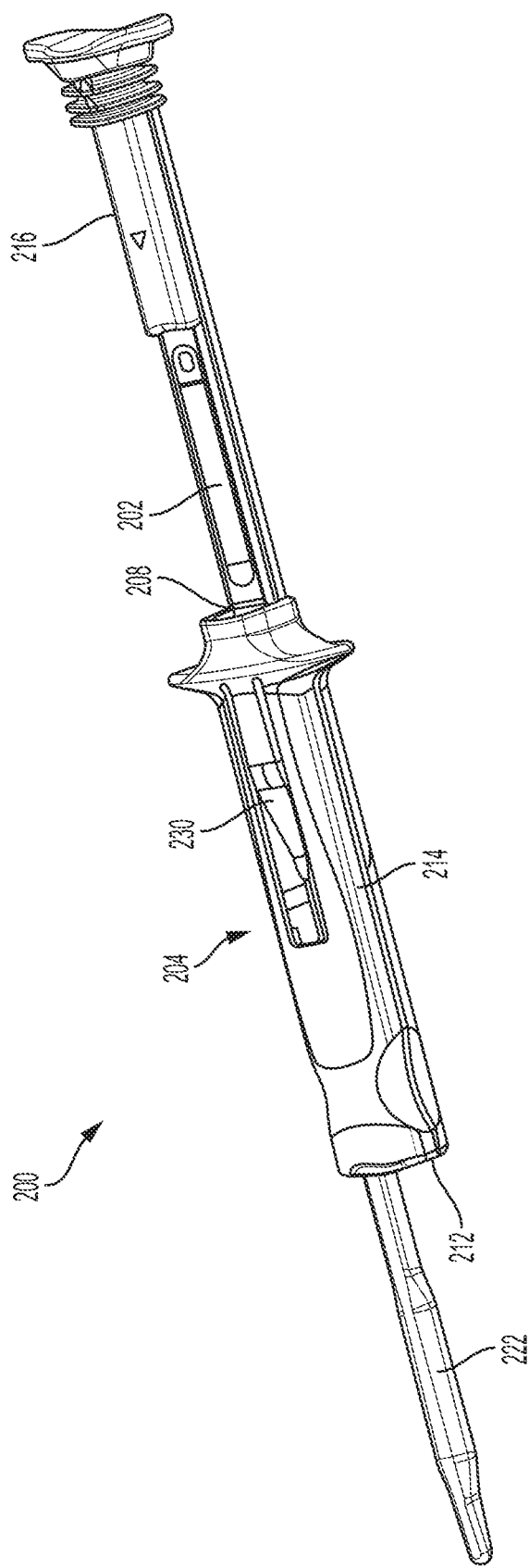
FIG. 2 shows an illustration of another exemplary introducer apparatus and an implantable medical device.

FIG. 2 shows an illustration of another exemplary introducer apparatus 200 and an implantable medical device 202. The introducer apparatus 200 includes a housing 204 having a proximal opening 208, a distal opening 212, and an intermediate portion 214 between the proximal opening 208 and the distal opening 212. The intermediate portion 214 is sized and configured to contain the implantable medical device 202.

The introducer apparatus 200 also includes an ejection rod 216 that is configured to pass through the proximal opening 208 and configured to eject the implantable medical device 202 from the housing 204 after the implantable medical device 202 has been arranged within the housing 204. As discussed in further detail below, the internal structure of the housing 204, including the intermediate portion 214, provides a pathway for the implantable medical device 202 and the ejection rod 216. The housing 204 may also include a clip 230 that extends into the internal structure of the intermediate portion 214 to hold the implantable medical device 202 within the housing 204 after the implantable medical device 202 is arranged through the proximal opening 208. The clip 230 may hold the implantable medical device 202 within the internal structure of the housing 204 above a pathway for the ejection rod 216. In addition, the clip 230 may be a flexible portion of an upper side of the housing that may be configured to deflect to release the implantable medical device toward the distal opening 212.

The introducer apparatus 200 also includes an inserter 222 that is configured to create a pocket sized to surround the implantable medical device 202 within the patient. The implantable medical device 202 may be guided into the pocket in response to the ejection rod 216 ejecting the implantable medical device from the housing 204 through the distal opening 212.

Prior to ejecting the implantable medical device 202 into the pocket, the implantable medical device 202 is arranged in position for the ejection rod 216 to eject the implantable medical device 202 from the housing 204. When the housing 204 includes the clip 230, the implantable medical device 202 may be released from the clip 230 to arrange the implantable medical device 202 in the pathway of the ejection rod 216. The pathway for the ejection rod 216 is aligned with the distal opening 212 to eject the implantable medical device 202 from the housing 204 through the distal opening 212. To facilitate use of the introducer apparatus 200, the housing 204 may include a stop (not shown) near or adjacent to the distal opening 212 to position the implantable medical device 202 adjacent the distal opening 212 prior to ejection. In addition and as discussed in further detail below, the stop protects against deployment or ejection of the implantable medical device 202 before the user of the introducer apparatus 202 moves the ejection rod 216 to eject the implantable medical device 202.

Figure 3A:
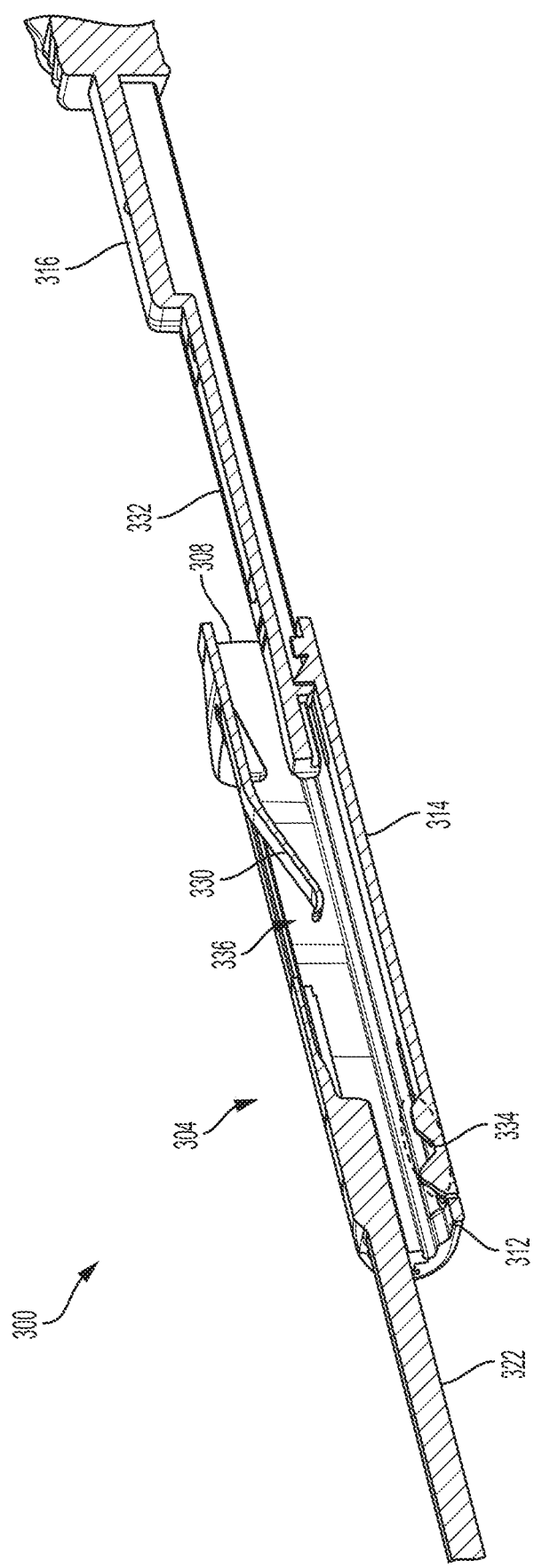
FIG. 3A shows a first cross-sectional illustration of another exemplary introducer apparatus.

FIG. 3A shows a first cross-sectional illustration of another exemplary introducer apparatus 300. The introducer apparatus 300 may be for positioning an implantable medical device (not shown) within a patient. The introducer apparatus 300 includes a housing 304 having a proximal opening 308, a distal opening 312, and an intermediate portion 314 between the proximal opening 308 and the distal opening 312. The intermediate portion 314 is sized and configured to contain the implantable medical device.

The introducer apparatus 300 also includes an ejection rod 316 that is configured to pass through the proximal opening 308 and configured to eject the implantable medical device from the housing 304 after the implantable medical device 202 has been arranged within the housing 304. As discussed in further detail below, an internal portion 336 of the housing 304, including the intermediate portion 314, provides a pathway for the implantable medical device and the ejection rod 316. The housing 304 may also include a clip 330 that extends into the internal portion 336 of the intermediate portion 314 to hold the implantable medical device within the housing 304 after the implantable medical device is arranged through the proximal opening 308. The clip 330 may hold the implantable medical device within the internal structure of the housing 304 above a pathway for the ejection rod 316.

Prior to ejecting the implantable medical device into the pocket, the implantable medical device is arranged in position for the ejection rod 316 to eject the implantable medical device from the housing 304. The pathway for the ejection rod 316 is aligned with the distal opening 312 to eject the implantable medical device 202 from the housing 304 through the distal opening 312. To facilitate positioning of the implantable medical device, the housing 304 may be configured to position the implantable medical device adjacent the distal opening 312 prior to ejection. In certain instances, the housing 304 may include structures (e.g., a stop 334) near or adjacent to the distal opening 312.

The housing 304 (e.g., the stop 334) may be configured to position the implantable medical device adjacent the distal opening 312 prior to ejection. The stop 334 may be configured to protect against deployment or ejection of the implantable medical device before the user of the introducer apparatus 202 intends to eject or deploy the implantable medical device by moving the ejection rod 316.

Figure 3B:
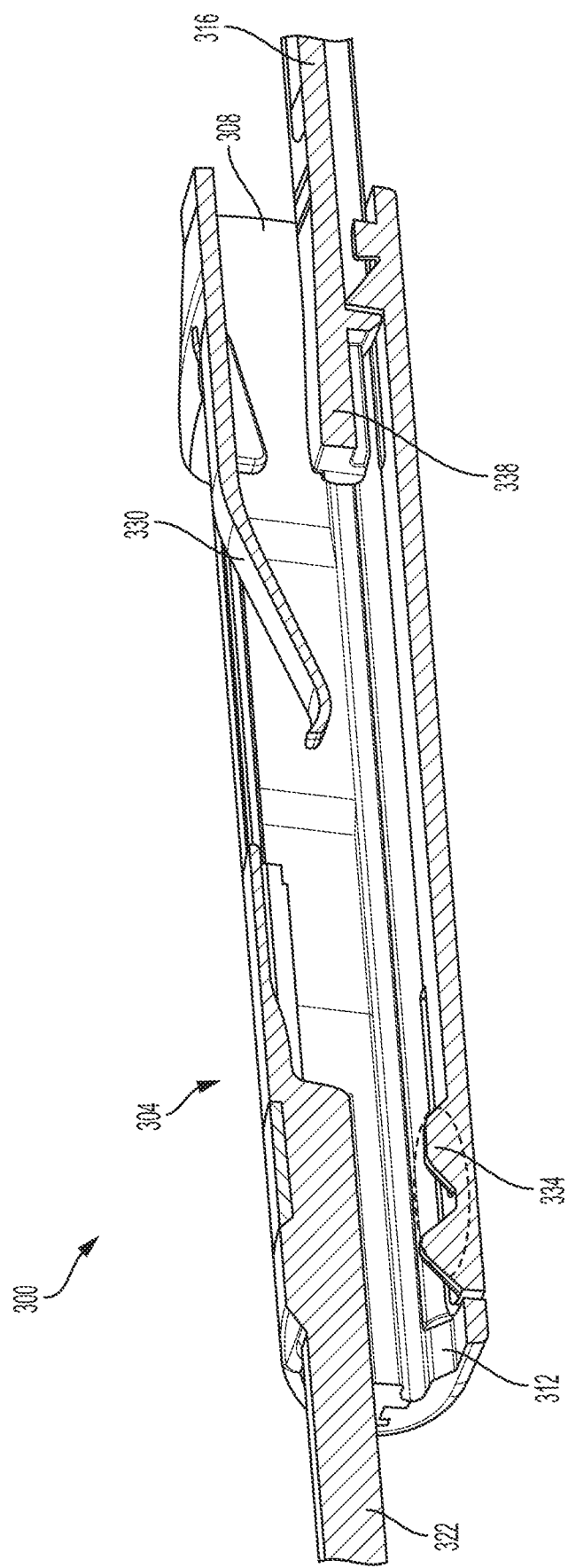
FIG. 3B shows a second cross-sectional view of the exemplary introducer apparatus shown in FIG. 3A.

FIG. 3B shows a second cross-sectional view of the exemplary introducer apparatus 300 shown in FIG. 3A. In certain instances, the housing 304, by way of the stop 334, is configured to maintain the implantable medical device adjacent the distal opening 312 and release the implantable medical device in response to a force applied by the ejection rod 316 that is strong enough to push the ejection rod over the stop 334 and to disengage the clip 330 from the implantable medical device. In embodiments, the housing 304 may include one or more raised surfaces in the form of the stop 334. In certain instances, the stop 334 is configured to position the implantable medical device adjacent the distal opening 312 prior to ejection. In certain instances, the stop 334 includes two curved surfaces. In addition, the one or more raised surfaces may include a single curved surface (e.g., a hump) or two curved surfaces. In instances where the stop 334 includes two curved surfaces, one of the curved surfaces may have a greater height than the other of the curved surfaces.

In certain instances, and in addition to positioning the implantable medical device, the stop 334 may also be configured to maintain positioning of the ejection rod 316 within the housing 304 prior to loading of the implantable medical device. The ejection rod 316 may be positioned through the proximal opening 308 and toward the distal opening 312 prior to loading of the implantable medical device. Arranging the ejection rod 316 in this manner may facilitate the introducer apparatus 300 being provided in a compact arrangement (e.g., for packaging). The stop 334 may hold a distal end 338 of the ejection rod 316 adjacent the distal opening 312 prior to a user applying a force to withdrawn the ejection rod 316 for loading the implantable medical device. The implantable medical device may be placed along surface 332 of the ejection rod 316 and loaded through the proximal opening 308 when the ejection rod 316 is withdrawn as shown in FIG. 3A.

The introducer apparatus 300 also includes an inserter 322 that is configured to create a pocket sized to surround the implantable medical device within the patient. The implantable medical device may be guided into the pocket in response to the ejection rod 316 ejecting the implantable medical device from the housing 304 through the distal opening 312. The stop 334 is configured to hold the implantable medical device adjacent the inserter 322 and release the medical device in response to a force applied by the ejection rod 316.

In certain instances, the stop 334 is configured to bias the implantable medical device toward the inserter 322 in response to the force applied by the ejection rod 316 to release the implantable medical device through the distal opening 312 of the housing 304. In certain instances, the stop 334 is arranged along a first surface of the internal portion 336 and the inserter 322 is arranged along and extends from another of surfaces of the internal portion 336.

The stop 334 facilitates placement of the implantable medical device for ejection from the housing 304 prior to desired implantation. In addition, the stop 334 positions the implantable medical device adjacent the distal opening 312 and thereby positions the implantable medical device near the inserter 322 leading into the incision. Further, the one or more raised surfaces (or stop 334) may facilitate arrangement of the ejection rod 316 until the user is ready to load the implantable medical device.

Figure 4A:
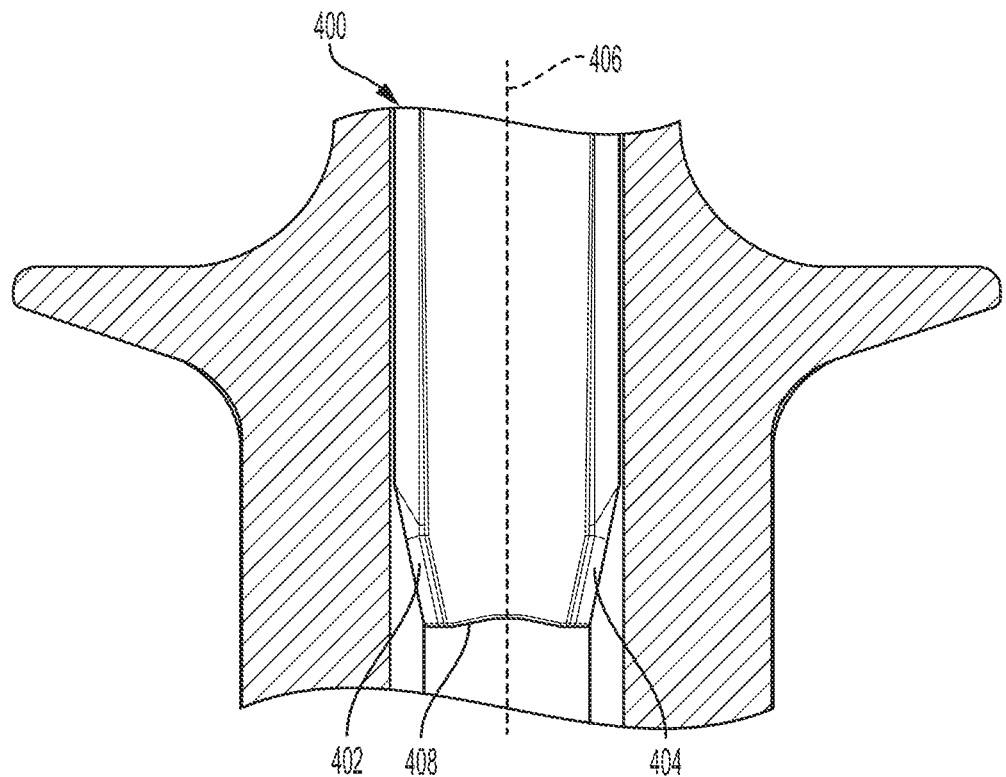
FIG. 4A shows a top view illustration of an example ejection rod used with an introducer apparatus.

FIG. 4A shows a cross-sectional top view illustration of an example ejection rod 400 used with an introducer apparatus. The ejection rod 400 may be used within any of the introducer apparatuses disclosed herein (e.g., as shown in FIGS. 1, 2, 3A-B, and FIG. 5). The ejection rod 400 may include two laterally opposing surfaces 402, 404 tapering inwardly toward a longitudinal axis 406 of the ejection rod 400. As discussed in further detail above, the ejection rod 400 is configured to pass a housing of an introducer apparatus to eject an implantable medical device from the introducer apparatus. As shown in FIG. 4A, a distal end 408 of the ejection rod 400 may include a curved surface configured to interface with a corresponding surface of the implantable medical device.

Figure 4B:
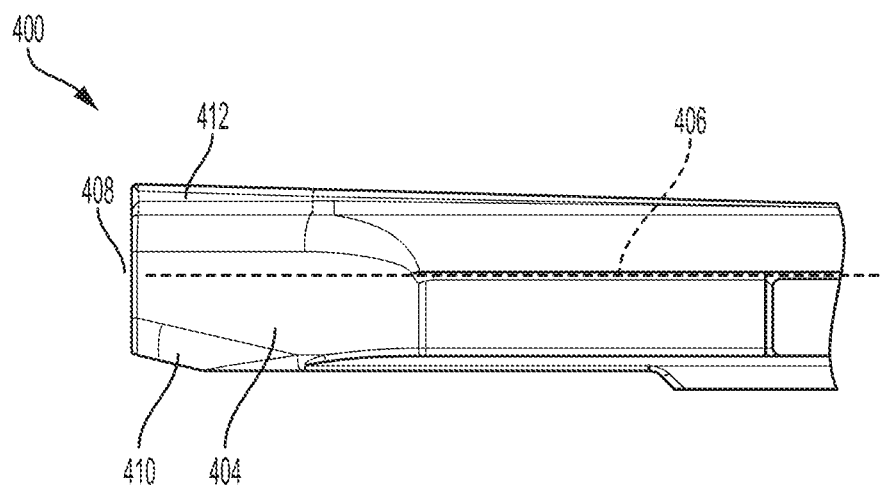
FIG. 4B shows a side cross-sectional view of the example ejection rod shown in FIG. 4A.

FIG. 4B shows a cross-sectional side view of the example ejection rod 400 shown in FIG. 4A. In certain instances, the ejection rod 400 also includes a bottom surface 410 that tapers inwardly reducing a diameter or thickness of the ejection rod 400. In certain instances, a top surface 412 of the ejection rod is approximately planar, or the top surface 412 may taper upwardly in the distal direction increasing a diameter or thickness of the ejection rod 400.

The ejection rod 400 having three tapered surfaces as shown in FIGS. 4A-B may reduce the likelihood of the ejection rod 400 catching on a patient's skin when the ejection rod 400 ejects an implantable medical device from an introducer apparatus into a pocket as discussed above. In addition, the three tapered surfaces of the ejection rod 400 may facilitate smoother implantation and facilitate implantation of the implantable medical device deeper into the created pocket and away from the incision.

Figure 5:
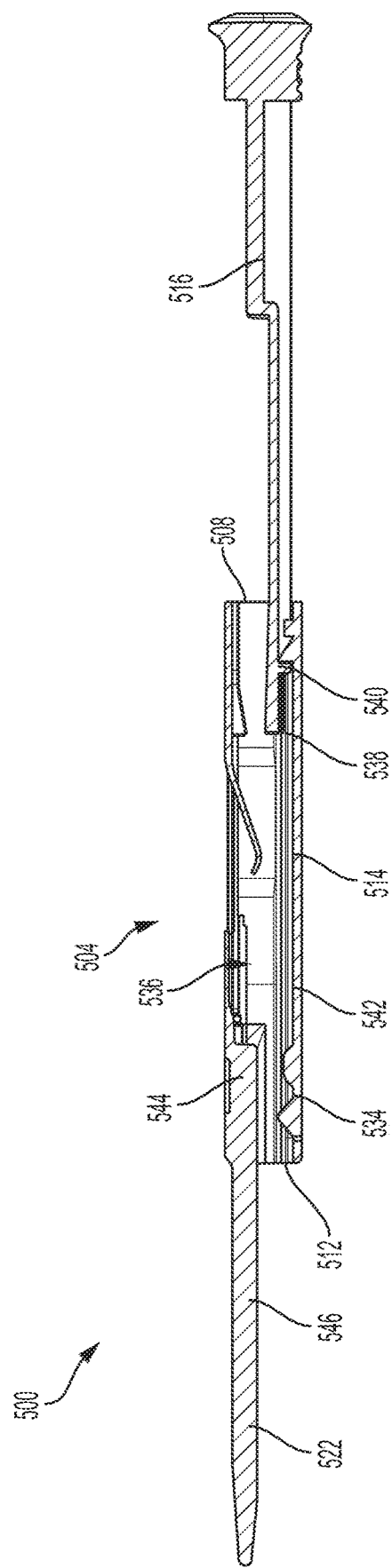
FIG. 5 shows a cross-sectional illustration of another exemplary introducer apparatus.

FIG. 5 shows a cross-sectional illustration of another exemplary introducer apparatus 500. The introducer apparatus 500 may be for positioning an implantable medical device (not shown) within a patient. The introducer apparatus 500 includes a housing 504 having a proximal opening 508, a distal opening 512, and an intermediate portion 514 between the proximal opening 508 and the distal opening 512. The intermediate portion 514 is sized and configured to contain the implantable medical device.

The introducer apparatus 500 also includes an ejection rod 516 that is configured to pass through the proximal opening 508 and configured to eject the implantable medical device from the housing 504 after the implantable medical device 202 has been arranged within the housing 504. As discussed in further detail below, an internal portion 536 of the housing 504, including the intermediate portion 514, provides a pathway for the implantable medical device and the ejection rod 516.

Prior to ejecting the implantable medical device into the pocket, the implantable medical device is arranged in position for the ejection rod 516 to eject the implantable medical device from the housing 504. The pathway for the ejection rod 516 is aligned with the distal opening 512 to eject the implantable medical device 202 from the housing 504 through the distal opening 512. To facilitate positioning of the implantable medical device, the housing 504 may include a stop 534 that is configured to position the implantable medical device adjacent the distal opening 512 prior to ejection.

By way of the stop 534 being configured to position the implantable medical device adjacent the distal opening 512 prior to ejection, the stop 534 is configured to protect against deployment or ejection of the implantable medical device before the user of the introducer apparatus 502 intending to eject or deploy the implantable medical device by moving the ejection rod 516. In certain instances, the stop 534 is configured to maintain the implantable medical device adjacent the distal opening 512 and release the implantable medical device in response to a force applied by the ejection rod 516.

In certain instances, the stop 534 may include one or more raised surfaces. In certain instances, the one or more raised surfaces of the stop 534 are configured to position the implantable medical device adjacent the distal opening 512 prior to ejection. In certain instances, the one or more raised surfaces of the stop 534 include two curved surfaces. In addition, the one or more raised surfaces may include a single curved surface (e.g., a hump) or two curved surfaces. In instances where the one or more raised surfaces of the stop 534 include two curved surfaces, one of the curved surfaces may have a greater height than the other of the curved surfaces.

In certain instances, the stop 534 may also be configured to maintain positioning of the ejection rod 516 within the housing 504 prior to loading of the implantable medical device. The ejection rod 516, for example, may be positioned through the proximal opening 508 and toward the distal opening 512 prior to loading of the implantable medical device. Arranging the ejection rod 516 in this manner may facilitate the introducer apparatus 500 being provided in a compact arrangement (e.g., for packaging). The one or more raised surfaces of stop 534 may hold a distal end 538 of the ejection rod 516 adjacent the distal opening 512 prior to a user applying a force to withdrawn the ejection rod 516 for loading the implantable medical device. in certain instances, the ejection rod 516 includes a projection 540 that may be arranged between the two raised surfaces of the stop 534 to hold a distal end 538 of the ejection rod 516 adjacent the distal opening 512.

The introducer apparatus 500 also includes an inserter 522 that is configured to create a pocket sized to surround the implantable medical device within the patient. The implantable medical device may be guided into the pocket in response to the ejection rod 516 ejecting the implantable medical device from the housing 504 through the distal opening 512. The stop 534, in certain instances, is configured to hold the implantable medical device adjacent the inserter 522 and release the medical device in response to a force applied by the ejection rod 516.

In certain instances, the one or more raised surfaces of the stop 534 are configured to bias the implantable medical device toward the inserter 522 in response to the force applied by the ejection rod 516 to release the implantable medical device through the distal opening 512 of the housing 504. In certain instances, the one or more raised surfaces of the stop 534 are arranged along a first surface 542 of the internal portion 536 and a bottom surface 546 of the inserter 522 is arranged along and extends from a second surface 544 of the internal portion 536 of the intermediate portion 514. The one or more raised surfaces of stop 534 facilitate placement of the implantable medical device during ejection from the housing 504 by forcing the implantable medical device toward the inserter 522, which forms a pocket in the patient. prior to desired implantation.

The one or more raised surfaces (or stop 534) facilitate placement of the implantable medical device for ejection from the housing 504 prior to desired implantation. In addition, the one or more raised surfaces (or stop 534) positions the implantable medical device adjacent the distal opening 512 and thereby positions the implantable medical device near the inserter 522 leading into the incision. Further, the one or more raised surfaces (or stop 534) may facilitate arrangement of the ejection rod 516 until the user is ready to load the implantable medical device. In addition, the one or more raised surfaces of the stop 534 positions the implantable medical device adjacent the distal opening 512 and thereby positions the implantable medical device near the inserter 522 leading into the incision. Further, the one or more raised surfaces of the stop 534 may facilitate arrangement of the ejection rod 516 until the user is ready to load the implantable medical device.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the subject matter described herein is intended to embrace all such alternatives, modifications, and variations as fall within the scope of the claims, together with all equivalents thereof.

We claim:

1. An introducer apparatus for positioning an implantable medical device within a patient, the introducer apparatus comprising:

a housing having a proximal opening and a distal opening and an intermediate portion sized to contain the implantable medical device, the housing having a clip extending from the housing into the intermediate portion, the clip configured to hold the implantable medical device within the housing, and the intermediate portion including a stop extending from the housing and into the intermediate portion, the stop configured to position the implantable medical device adjacent the distal opening prior to ejection;

an ejection rod configured to pass through the proximal opening and eject the implantable medical device from the housing through the distal opening of the housing; and an inserter arranged at and extending from a distal portion of the housing, wherein the stop is configured to hold the implantable medical device adjacent the inserter and release the implantable medical device in response to a force applied by the ejection rod.

2. The apparatus of claim 1, wherein the stop includes one or more raised surfaces configured to position the implantable medical device adjacent the distal opening prior to ejection.

3. The apparatus of claim 2, wherein the intermediate portion includes a first surface and a second surface, and one of the first surface and the second surface includes the stop.

4. The apparatus of claim 3, wherein the stop is configured to maintain positioning of the ejection rod within the housing prior to loading of the implantable medical device.

5. The apparatus of claim 4, wherein the stop is configured to maintain a distal portion of the ejection rod adjacent the distal opening prior to withdrawal of the ejection rod toward the proximal opening for loading of the implantable medical device.

6. The apparatus of claim 5, wherein the stop includes two raised portions and the two raised portions are configured to maintain a distal portion of the ejection rod between the raised portions prior to withdrawal of the ejection rod toward the proximal opening for loading of the implantable medical device.

7. The apparatus of claim 3, wherein the stop includes two curved surfaces and one of the curved surfaces has a greater height than the other of the curved surfaces.

8. The apparatus of claim 1, wherein the stop is configured to bias the implantable medical device toward the inserter in response to the force applied by the ejection rod to release the implantable medical device through the distal opening of the housing.

9. The apparatus of claim 1, wherein the stop is configured to maintain the implantable medical device adjacent the distal opening and release the implantable medical device in response to a force applied by the ejection rod.

10. An introducer apparatus for positioning an implantable medical device within a patient, the introducer apparatus comprising:

a housing having a proximal opening and a distal opening and an intermediate portion sized to contain the implantable medical device, the housing having a clip extending into the intermediate portion configured to hold the implantable medical device within the housing, and the intermediate portion including a stop configured to position the implantable medical device adjacent the distal opening prior to ejection;

an ejection rod including two laterally opposing surfaces tapering inwardly toward a longitudinally axis of the ejection rod and configured to pass through the proximal opening and eject the implantable medical device from the housing through the distal opening of the housing; and an inserter arranged at and extending from a distal portion of the housing, wherein the stop is configured to hold the implantable medical device adjacent the inserter and release the implantable medical device in response to a force applied by the ejection rod.

11. The apparatus of claim 10, wherein a bottom surface of the ejection rod is tapered inwardly reducing a diameter of the ejection rod.

12. The apparatus of claim 11, wherein the intermediate portion includes a first surface and a second surface, wherein the second surface includes the stop and the bottom surface of the ejection rod is adjacent the second surface of the intermediate portion of the housing.

13. The apparatus of claim 10, wherein the inserter is arranged along the first surface and the stop is configured to bias the implantable medical device toward the inserter in response to the force applied by the ejection rod to release the implantable medical device through the distal opening of the housing.

14. The apparatus of claim 13, wherein a top surface of the ejection rod is substantially planar.

15. The apparatus of claim 10, wherein the stop includes one or more raised surfaces configured to position the implantable medical device adjacent the distal opening prior to ejection.

16. A method comprising:

arranging an implantable medical device within an introducer, the introducer including:

a housing having a proximal opening and a distal opening and an intermediate portion, the housing having a clip extending from the housing into the intermediate portion, the clip configured to hold the implantable medical device within the housing, and the intermediate portion including a stop extending from the housing and into the intermediate portion, the stop configured to position the implantable medical device adjacent the distal opening prior to ejection;

an ejection rod configured to pass through the proximal opening; and an inserter arranged at and extending from a distal portion of the housing, wherein the stop is configured to hold the implantable medical device adjacent the inserter and release the implantable medical device in response to a force applied by the ejection rod;

arranging the implantable medical device to contact the stop adjacent to the distal opening; and passing the implantable medical device over the stop and ejecting the implantable medical device from the housing through the distal opening of the housing.

17. The method of claim 16, further comprising withdrawing the ejection rod distally from the stop prior to arranging the implantable medical device within the introducer.

* * * * *